United States Patent [19]

Melder et al.

[11] Patent Number: 5,663,444
[45] Date of Patent: Sep. 2, 1997

[54] PREPARATION OF A PURE DIALKYLAMINOETHANOL STABLE AGAINST DISCOLORATION

[75] Inventors: Johann-Peter Melder, Mannheim; Günther Ruider, Wachenheim; Tom Witzel, Ludwigshafen; Karl-Heinz Ross, Grünstadt; Günter Boettger, Bad Dürkheim, all of Germany

[73] Assignee: BASF Aktiengesellschaft, Ludwigshafen, Germany

[21] Appl. No.: 497,072

[22] Filed: Jun. 30, 1995

[51] Int. Cl.$^6$ .................................................. C07C 209/02
[52] U.S. Cl. .................................................. 564/477
[58] Field of Search .................................. 564/477, 475, 564/503

[56] References Cited

U.S. PATENT DOCUMENTS

| | | |
|---|---|---|
| 2,337,004 | 12/1943 | Schwoegler . |
| 2,373,199 | 4/1945 | Schwoegler et al. . |
| 3,131,132 | 4/1964 | Moss et al. . |
| 3,567,779 | 3/1971 | Currier et al. . |
| 4,223,138 | 9/1980 | Schubart .................. 544/162 |
| 4,379,024 | 4/1983 | Gardner . |

FOREIGN PATENT DOCUMENTS

| | | |
|---|---|---|
| 2387212 | 11/1978 | France . |
| 203534 | 10/1983 | Germany . |
| 1-160947 | 12/1987 | Japan . |
| 1479747 | 7/1977 | United Kingdom . |

OTHER PUBLICATIONS

Houben/weyl, Methoden der organischen Chemie, vol. 11/1, pp. 311-350 (1957).

Helvetica Chimica Acta, vol. 52, pp. 408-418 (1969).

Primary Examiner—Brian M. Burn
Attorney, Agent, or Firm—John H. Shurtleff

[57] ABSTRACT

A process for the preparation of a color-stable dialkylaminoethanol of the formula

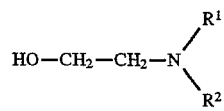

in which $R^1$ and $R^2$ independently are $C_1$–$C_{20}$-alkyl, by reacting ethylene oxide with a dialkylamine of the formula $HNR^1R^2$, in which $R^1$ and $R^2$ have the same meaning, in the presence of from 2.5 to 50% by weight of water, based on the reaction mixture, at a temperature of from 95° to 170° C., and separating off the water and high-boiling constituents by distillation under a reduced pressure and at a temperature of from 40° to 90° C. at the column bottom.

15 Claims, No Drawings

PREPARATION OF A PURE DIALKYLAMINOETHANOL STABLE AGAINST DISCOLORATION

The present invention relates to a process for the preparation of a dialkylaminoethanol by reacting a dialkylamine and ethylene oxide in the presence of from 2.5 to 50% by weight of water at elevated temperature and separating off the dialkylamine by distillation at up to 90° C. at the column bottom.

Alkylaminoethanols are important intermediates for the chemical and pharmaceutical industries. Dimethylaminoethanol is employed, for example in the form of salts, soaps, ethers and esters, in a wide variety of sectors, as an emulsifier and surface-active substance and as a catalyst in polyurethane chemistry. In the pharmaceutical industry it is used to synthesize active compounds (tranquilizers, antihistamines and analgesics). For most applications, discoloration in the dimethylaminoethanol is unwanted.

The addition of amines onto ethylene oxide is, as in the case of ammonia, accelerated considerably by addition of water. Thus, the reaction of ethylene oxide with dimethylamine in the absence of water requires heating for a number of hours at 150° C., whereas these components combine to give dimethylaminoethanol even without heating if an aqueous dimethylamine solution is used. An activity similar to that of the water is also possessed by alcohols such as methanol or ethanol (Houben-Weyl, Methoden der organischen Chemie, Volume 11/1, 1957, 311–350).

It is known that alkanol amines react further, by ethoxylation of the hydroxyl group, to give products with higher degrees of ethoxylation. This follow-on reaction is said to be favored by water but can be substantially suppressed by using excess amine (from 1.1:1 to 4:1) (DE-A-23 57 076; DD-A-203 534, U.S. Pat. No. 2,337,004, U.S. Pat. No. 2,373,199).

It is also known that tertiary amines such as, for example, dimethylaminoethanol react with oxiranes at below 80° C. in both the absence and the presence of water to give thermally unstable quaternary ammonium compounds which decompose fairly quickly above 90° C. (E. Tobler et al., Helv. Chim. Acta 52, 1969, 408–418).

EP-A-70 978 discloses the continuous reaction of excess dimethylamine (2.2 eq) with ethylene oxide in the presence of water (from 0.2 to 0.5 eq) at 150° C. and subsequent distillative working up with the addition of defined amounts of sodium borohydride.

U.S. Pat. No. 3,131,132 discloses the batchwise reaction of excess dimethylamine (from 1 to 2 eq) with ethylene oxide in the presence of water (from 3 to 15 eq) at from 50° to 100° C. and subsequent distillative working up (190 mbar) after adjustment of the pH to 11.5.

JP-A-01/160 947 discloses the water-catalyzed synthesis of dimethylethanolamine and subsequent working up by the distillative removal of high-boiling constituents (100 mbar), hydrogenation of the distillate over Ru/C and fine distillation at 100 mbar.

DD-A-203 534 discloses the reaction of excess dimethylamine (from 1.1 to 3.5:1) with ethylene oxide in the presence of catalytic amounts of water (from 0.02 to 0.15 eq) under very mild reaction conditions (from 50° to 90° C.) and subsequent distillative working up with a still temperature of not more than 90° C.

Reducing the reaction temperature to below 90° C. leads, according to Helv. Chim. Acta 52, 1969, 408–418, to the formation of quaternary bases, leading to losses in yield.

U.S. Pat. No. 3,567,779 discloses how the discoloration can be inhibited by addition of mono- or diethanolamine to dimethylethanolamine.

The abovementioned solutions for obtaining a stable-colored dialkylethanolamine have the disadvantages of the addition of a foreign stabilizer, which contaminates the dialkylethanolamines, or of a purifying substance (reducing agent or acid) whose quantitative removal is possible only at great expense.

It is an object of the present invention to remedy the above-mentioned disadvantages.

We have found that this object is achieved by a novel and improved process for the preparation of stable-colored dialkylaminoethanol of the general formula I

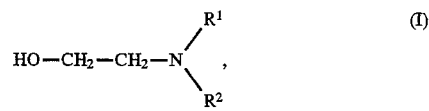

in which $R^1$ and $R^2$ independently are $C_1$–$C_{20}$-alkyl, from dialkylamine of the general formula II

in which $R^1$ and $R^2$ are as defined above, and ethylene oxide, which comprises carrying out the reaction in the presence of from 2.5 to 50% by weight of water at from 95° to 170° C. and separating off the water and high-boiling constituents by distillation at from 40° to 90° C. at the column bottom.

The process according to the invention can be carried out as follows: the reaction of dialkylamines II in which $R^1$ and $R^2$ independently are $C_1$–$C_{20}$-alkyl, preferably $C$–$C_8$-alkyl, particularly preferably $C_1$–$C_4$-alkyl and, in particular, methyl or ethyl, very particularly methyl, with ethylene oxide can be carried out by a continuous or batchwise procedure at from 90° to 160° C., preferably from 100° to 140° C., and at from 1.5 to 100 bar, preferably from 5 to 70 bar and with particular preference from 10 to 40 bar, in the presence of from 2.5 to 50% by weight, preferably from 5 to 35% by weight and with particular preference from 8 to 25% by weight, of water, based on the reaction mixture.

The molar ratio of dialkylamine II to ethylene oxide is generally from 1:1 to 50:1, preferably from 1.1:1 to 20:1 and with particular preference from 1.2:1 to 10:1.

Excess dialkylamine is removed by distillation and preferably recycled to the process. The distillative removal of water and high-boiling by-products (quaternary bases, dialkylaminodiglycol) is accomplished at from 40° to 90° C., preferably from 55° to 90° C. and with particular preference from 60° to 85° C. at the column bottom and at from 5 to 150 mbar, preferably from 25 to 150 mbar and with particular preference from 50 to 150 mbar.

The dialkylethanolamines which are obtainable by the process according to the invention have a degree of purity which is generally from 99 to 99.999%, preferably from 99.5 to 99.99% and with particular preference from 99.8 to 99.9% and are stable to discoloration for months when stored under an inert gas atmosphere (nitrogen, argon).

EXAMPLES

Examples 1 and 2 which follow illustrate the process according to DE-A-203,534 which demonstrates the suppression of the undesired ethoxylation of the hydroxyl group by using excess amine and lower reaction temperatures.

Example 1

99 g (2.2 mol) of dimethylamine and 1.1 g (0.06 mol) of water are introduced into a 300 ml stirred reactor made from V2A-grade steel and equipped with pressure and temperature indicators and are preheated to 65° C. With the stirrer mechanism operating, 5 g of ethylene oxide are first of all metered into the liquid phase, and after a few minutes the commencement of the reaction is indicated by a temperature increase. The remaining quantity of a total of 48 g (1.1 mol) of ethylene oxide is then metered in over the course of 60 min. By external cooling the reaction is held at between 74° and 80° C. After the end of metering stirring is continued for 5 minutes, the reaction mixture is cooled to 50° C., the reactor is let down carefully and excess DMA is removed by $N_2$ stripping at 50° C., to give 93.0 g of ethylene oxide-free reaction product having the following composition:

Dimethylethanolamine: 80.52%
Dimethylaminodiglycol: 5.28%
Quaternary bases: 10.00%
Other products: 3.10%
Water: 1.10%

Distillation of the crude product using a 35 cm packed column under a reduced pressure of 50–100 mbar gives DMEA having a color number of 5 APHA. The color stability is assessed in the following test: the color number is determined after heating pure DMEA at 60° C. for 6 h under nitrogen: 5 APHA.

Example 2

99 g (2.2 mol) of dimethylamine and 1.1 g (0.06 mol) of water are introduced into a 300 ml stirred reactor made from V2A-grade steel and equipped with pressure and temperature indicators and are preheated to 65° C. With the stirrer mechanism operating, 5 g of ethylene oxide are first of all metered into the liquid phase, and after a few minutes the commencement of the reaction is indicated by a temperature increase. The remaining quantity of a total of 48 g (1.1 mol) of ethylene oxide is then metered in over the course of 120 min. By external cooling the reaction is held at between 74° and 80° C. After the end of metering stirring is continued for 5 minutes, the reaction mixture is cooled to 50° C., the reactor is let down carefully and excess DMA is removed by $N_2$ stripping at 50° C., to give 95.0 g of ethylene oxide-free reaction product having the following composition:

Dimethylethanolamine: 87.17%
Dimethylaminodiglycol: 3.28%
Quaternary bases: 5.63%
Other products: 2.82%
Water: 1.10%

Distillation of the crude product using a 35 cm packed column under a reduced pressure of 50–100 mbar gives DMEA having a color number of 5 APHA. Color number after 6 h/60° C.: 5 APHA.

Example 3

In a 500 ml reaction tube with pressure and temperature indicators, a preheated mixture at 75° C. of dimethylamine (3350 g/h; 74.5 mol/h) and water (840 g/h; 46.7 mol/h) is reacted continuously with 600 g/h (13.6 mol/h) of ethylene oxide. External cooling is used to dissipate the heat of reaction so that 110° C. is not exceeded. Distillative removal and recycling of excess dimethylamine (3–4 bar/bottom temperature 130°–140° C.) and water (as an azeotrope with dimethylethanolamine; 600 mbar/bottom temperature 100°–105° C.) give 1275 g/h of ethylene oxide-free reaction product having the following composition:

Dimethylethanolamine: 82.64%
Dimethylaminodiglycol: 2.40%
Quaternary bases: 3.67%
Other products: 3.55%
Residual water: 7.74%

Distillative working up (removal of high-boiling constituents and residual water) at 50 mbar (bottom temperature 65°–75° C.) gives dimethylethanolamine in 99.8–99.9% purity with a color number of 5 APHA. Color number after 6 h/60° C.: 5 APHA; color number after 3 months at room temperature under nitrogen: 10 APHA.

Example 4

90 g (2 mol) of dimethylamine and 22.5 g (2.5 mol) of water are introduced into a 300 ml stirred reactor made of V2A-grade steel and having pressure and temperature indicators and are preheated to 120° C. With the stirrer mechanism operating, 22 g (0.5 mol) of ethylene oxide are then metered in over the course of 10 min, during which there is an increase to 140° C. After the end of metering stirring is continued at 140° C. for 5 minutes, the reaction mixture is cooled to 50° C., the reactor is let down and excess dimethylamine and some of the water are removed by $N_2$ stripping, to give 50.8 g of ethylene oxide-free reaction product having the following composition:

Dimethylethanolamine: 84.45% by weight
Dimethylaminodiglycol: 1.00% by weight
Quaternary bases: <0.10% by weight
Other products: 1.55% by weight
Residual water: 13.00% by weight Distillation of the crude product using a 35 cm packed column under a reduced pressure of 50 mbar gives DMEA having a color number of 5 APHA. Color number after 6 h/60° C.: 5 APHA.

We claim:

1. A process for the preparation of a color-stable dialkylaminoethanol of the formula

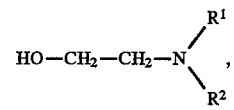

in which $R^1$ and $R^2$ independently are $C$–$C_{20}$-alkyl, which comprises:

reacting ethylene oxide with a dialkylamine of the formula

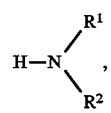

in which $R^1$ and $R^2$ are as defined above,
in the presence of from 2.5 to 50% by weight of water, based on the reaction mixture, at a temperature of from 95° to 170° C., and separating off the water and high-boiling constituents by distillation under a reduced pressure and at a temperature of from 40° to 90° C. at the column bottom.

2. The process as claimed in claim 1, wherein $R^1$ and $R^2$ are $C_1$–$C_8$-alkyl.

3. The process as claimed in claim 1, wherein $R^1$ and $R^2$ are $C_1$–$C_4$-alkyl.

4. The process as claimed in claim 1, wherein $R^1$ and $R^2$ are methyl or ethyl.

5. The process as claimed in claim 1, wherein $R^1$ and $R^2$ are methyl.

6. The process as claimed in claim 1, wherein water and high-boiling constituents are separated off by distillation at from 5 to 150 mbar and at from 40° to 90° C. at the column bottom.

7. The process as claimed in claim 1, wherein water and high-boiling constituents are separated off by distillation at from 25 to 150 mbar and at from 40° to 90° C. at the column bottom.

8. The process as claimed in claim 1, wherein dialkylamine II and ethylene oxide are reacted at from 100° to 140° C.

9. The process as claimed in claim 1, wherein the dialkylamine II is separated off by distillation at from 55° to 90° C. at the column bottom.

10. The process as claimed in claim 1, wherein water and high-boiling constituents are separated off by distillation at from 60° to 85° C. at the column bottom.

11. A process as claimed in claim 1, wherein the molar ratio of the dialkylamine II to ethylene oxide is from 1:1 to 50:1 and the excess of the dialkylamine is separated off at a temperature up to 140° C. at the column bottom.

12. A process as claimed in claim 11, wherein the molar ratio of the dialkylamine II to ethylene oxide is from 1.1:1 to 20:1.

13. A process as claimed in claim 11, wherein the molar ratio of the dialkylamine II to ethylene oxide is from 1.2:1 to 10:1.

14. A process as claimed in claim 11, wherein said excess dialkylamine is recyled to the reaction mixture and the process is carried out continuously.

15. A process as claimed in claim 14, wherein excess water as an azeotrope with said dialkylethanolamine is also continuously separated and recycled to the reaction mixture.

* * * * *

UNITED STATES PATENT AND TRADEMARK OFFICE
CERTIFICATE OF CORRECTION

PATENT NO. : 5,663,444
DATED : Sep. 2, 1997
INVENTOR(S) : Johann-Peter Melder, Günther Ruider, Tom Witzel, Karl-Heinz Ross and Günter Boettger It is certified that error appears in the above-indentified patent and that said Letters Patent is hereby corrected as shown below:

IN THE CLAIMS:

Claim 1. line 3 (following formula I): change "$C-C_{20}$" to -- $C_1-C_{20}$ --.

Signed and Sealed this

Nineteenth Day of May, 1998

Attest:

BRUCE LEHMAN

Attesting Officer

Commissioner of Patents and Trademarks